United States Patent
Kalke et al.

(10) Patent No.: US 11,020,079 B2
(45) Date of Patent: Jun. 1, 2021

(54) X-RAY IMAGING UNIT FOR X-RAY IMAGING

(71) Applicant: PaloDEx Group OY, Tuusula (FI)

(72) Inventors: Martti Kalke, Tuusula (FI); Esa Suuronen, Kerava (FI)

(73) Assignee: PALODEX GROUP OY, Tuusula (FI)

( * ) Notice: Subject to any disclaimer, the term of this patent is extended or adjusted under 35 U.S.C. 154(b) by 0 days.

(21) Appl. No.: 16/256,397

(22) Filed: Jan. 24, 2019

(65) Prior Publication Data

US 2019/0223821 A1    Jul. 25, 2019

(30) Foreign Application Priority Data

Jan. 24, 2018  (FI) ...................... 20185069

(51) Int. Cl.
| | |
|---|---|
| *A61B 6/03* | (2006.01) |
| *G06T 7/73* | (2017.01) |
| *G06T 11/00* | (2006.01) |
| *A61B 6/14* | (2006.01) |
| *A61B 6/00* | (2006.01) |

(52) U.S. Cl.
CPC ............. *A61B 6/54* (2013.01); *A61B 6/032* (2013.01); *A61B 6/14* (2013.01); *A61B 6/488* (2013.01); *A61B 6/501* (2013.01); *A61B 6/58* (2013.01); *G06T 7/74* (2017.01); *G06T 11/005* (2013.01); *A61B 6/4435* (2013.01); *G06T 2207/10081* (2013.01)

(58) Field of Classification Search
CPC .... G06T 7/73; G06T 7/74; G06T 7/70; G06T 2207/30196; A61B 6/589
See application file for complete search history.

(56) References Cited

U.S. PATENT DOCUMENTS

| | | | | |
|---|---|---|---|---|
| 5,921,927 | A | * | 7/1999 | McArdle ................. A61B 6/14 378/170 |
| 6,243,439 | B1 | | 6/2001 | Arai et al. |

(Continued)

FOREIGN PATENT DOCUMENTS

| | | |
|---|---|---|
| EP | 1815794 A1 | 8/2007 |
| EP | 2130491 A1 | 12/2009 |

OTHER PUBLICATIONS

Search Report received in Finnish Patent Application No. 20185069, dated Aug. 21, 2018 (2 pages).

(Continued)

*Primary Examiner* — Yara B Green
(74) *Attorney, Agent, or Firm* — Michael Best & Friedrich LLP

(57) ABSTRACT

The application relates to an X-ray imaging unit (100) for X-ray imaging. The unit comprise a processor part (372), a gantry part (120), an X-ray source part (124) for emitting X-rays, and an X-ray imaging detector part (126) for receiving the X-rays from the source part. The gantry part comprises the source and detector parts. The processor part is configured to control the source and detector parts in order to obtain (205, 216) an image data. The processor part is further configured to determine (208) at least one reference structure (235, 236) of a patient (201) from the image data and determine (212) a position of a head (237) of the patient on a grounds of the at least one reference structure.

18 Claims, 2 Drawing Sheets

(56) References Cited

U.S. PATENT DOCUMENTS

| | | | |
|---|---|---|---|
| 2009/0323891 A1* | 12/2009 | Borghese | A61B 6/14 378/20 |
| 2010/0061509 A1* | 3/2010 | D'Ambrosio | A61B 6/4458 378/62 |
| 2011/0123081 A1 | 5/2011 | Sebok et al. | |
| 2011/0129058 A1 | 6/2011 | Ulrici et al. | |
| 2012/0099697 A1* | 4/2012 | Helm | A61B 6/4405 378/4 |
| 2012/0106704 A1* | 5/2012 | Maurer, Jr. | A61N 5/1037 378/65 |
| 2013/0058556 A1 | 3/2013 | Ohishi et al. | |
| 2014/0221812 A1 | 8/2014 | Hesimann | |
| 2016/0081641 A1* | 3/2016 | Bouhnik | A61B 6/032 378/5 |
| 2016/0166205 A1 | 6/2016 | Ernst et al. | |
| 2016/0275679 A1 | 9/2016 | Im et al. | |
| 2018/0247427 A1* | 8/2018 | Geiger | G06K 9/00201 |

OTHER PUBLICATIONS

European Patent Office Search Report for Application No. 19152930. 4, dated Jun. 6, 2019, 9 pages.

* cited by examiner

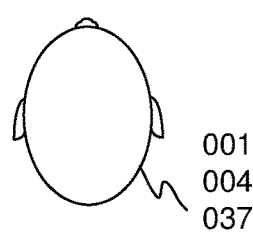
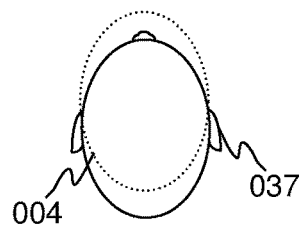
Fig. 4a
Fig. 4b
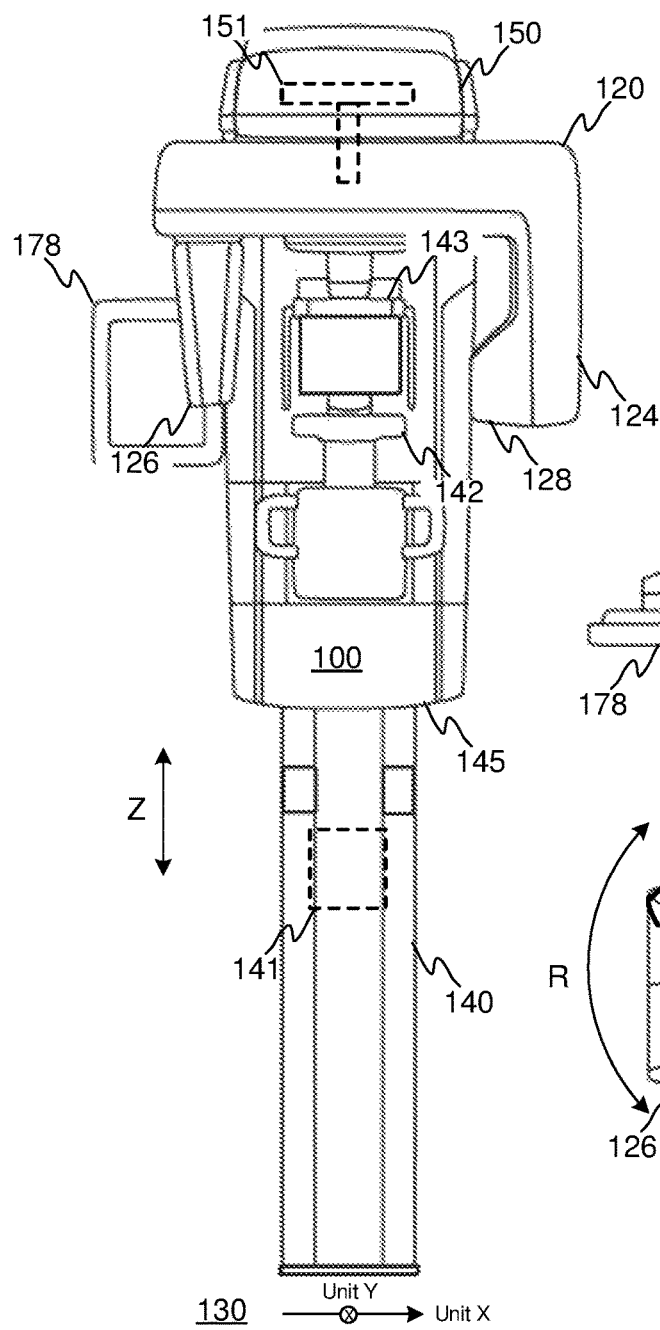
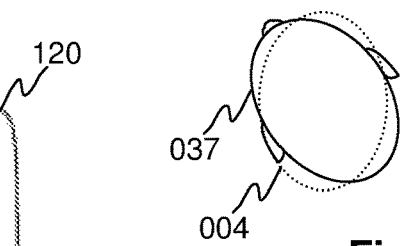
Fig. 4c
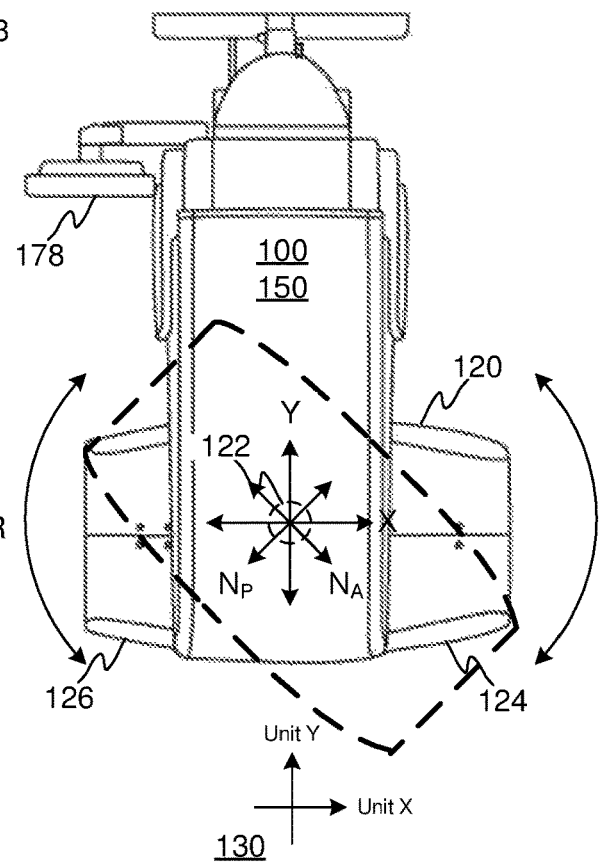
Fig. 1a
Fig. 1b

X-RAY IMAGING UNIT FOR X-RAY IMAGING

TECHNICAL FIELD

The application relates generally to an X-ray imaging unit for X-ray imaging.

BACKGROUND

FIG. 4a presents how a head 037 of a supported patient 001 to be imaged has been positioned correctly to an imaging position 004 for clinical Panoramic X-ray imaging. The correct positioning of the patient 037 is the most time consuming task of a user of an X-ray device in the imaging process.

In addition to the time consumption of the positioning, there is another problem relating to it when a false positioning of the patient 001 causes a significant fraction of a poor image quality.

FIG. 4b presents one misposition possibility when the patient 001 can be transitionally mispositioned, or he/she can move forward or backward after the correct positioning for some reason, according to the figure, whereupon the position of his/her head 037 differs transitionally from the correct position 004.

FIG. 4c presents another misposition possibility when the patient 001 can be rotationally mispositioned, or he/she can move, according to the figure so that the position of his/her head 037 differs rotationally from the correct position 004.

Naturally, the position of the patient 001 can comprise both transitional and rotational failures before the imaging.

A full-field (FF) Panoramic detector technology enables to select an anatomically correct layer with certain limitations. This is based on the fact that in FF-Panoramic systems a summing process is done in computer, not in a detector of the X-ray device, which allows to fix failures caused by the transitional misposition of the patient 001.

However, this process does not solve the problem of failures caused by the rotational misposition.

SUMMARY

One object of the invention is to provide an X-ray imaging method that withdraws the aforementioned drawbacks when translational and rotational errors in a positioning of a patient can be corrected before an actual scan by adjusting scan movements of an X-ray unit according to an actual position and angulation of the patient.

One object of the invention is fulfilled by an X-ray unit, a method, a computer program, and a computer-readable medium according to the independent claims.

One embodiment is an X-ray imaging unit for X-ray imaging, which comprises a processor part, a gantry part, an X-ray source part for emitting X-rays, and an X-ray imaging detector part for receiving the X-rays from the source part. The gantry part comprises the source and detector parts. The processor part is configured to control the source and detector parts in order to obtain an image data. The processor part is further configured to determine at least one reference structure of a patient from the image data and determine a position of a head of the patient on a grounds of the at least one reference structure.

One embodiment is a method for X-ray imaging by an X-ray imaging unit. The method comprises controlling, by means of a processor part, an X-ray source part and an X-ray imaging detector part in order to obtain an image data. The source part is configured to emit X-rays. The detector part is configured to receive the X-rays from the source part. The source and detector parts are embodied in a gantry part. The method further comprises determining, by means of the processor part, at least one reference structure of a patient from the image data and determining, by means of the processor part, a position of a head of the patient on a grounds of the at least one reference structure.

One embodiment is a computer program for X-ray imaging, which comprises controlling code for controlling, by means of a processor part, an X-ray source part and an X-ray imaging detector part in order to obtain an image data. The source part is configured to emit X-rays, The detector part is configured to receive the X-rays from the source part. The source and detector parts are embodied in a gantry part. The program further comprises determining code for determining, by means of the processor part, at least one reference structure of a patient from the image data and determining code for determining, by means of the processor part, a position of a head of the patient on a grounds of the at least one reference structure.

One embodiment is a tangible non-volatile computer-readable medium comprising a computer program for X-ray imaging. The program comprises controlling code for controlling, by means of a processor part, an X-ray source part and an X-ray imaging detector part in order to obtain an image data. The source part is configured to emit X-rays, The detector part is configured to receive the X-rays from the source part. The source and detector parts are embodied in a gantry part. The program further comprises determining code for determining, by means of the processor part, at least one reference structure of a patient from the image data and determining code for determining, by means of the processor part, a position of a head of the patient on a grounds of the at least one reference structure.

Further embodiments are presented in the dependent claims.

BRIEF DESCRIPTION OF THE FIGURES

The embodiments are presented with reference to the following figures:

FIG. 1a presents an X-ray imaging unit
FIG. 1b presents movements of the unit
FIG. 4a presents a correctly positioned head of a patient
FIG. 4b presents a transitionally mispositioned head
FIG. 4c presents a rotationally mispositioned head

DETAILED DESCRIPTION OF THE FIGURES

Figure 2A:
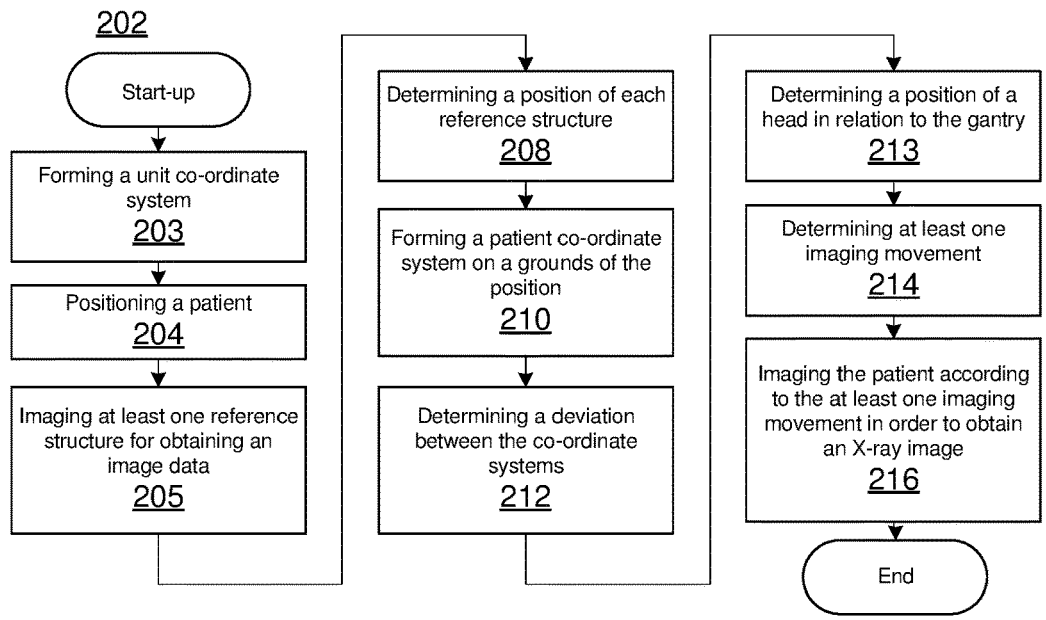
FIG. 2a presents a flowchart of X ray imaging method

FIG. 1a presents an X-ray imaging unit 100 for X-ray imaging an object (patient 201) in medical imaging.

The medical imaging can be extraoral dental imaging.

The unit 100 can be configured to perform a Panoramic and/or Computed Tomography (CT) imaging.

The unit 100 comprises a gantry part (rotator) 120 in order to image a Panoramic and/or CT image.

The gantry 120 embodies and supports an X-ray source part (head) 124 and an X-ray imaging detector part (head) 126.

The gantry 120 can have a form of letter C, whereupon the source part 124 can be attached on one end of the gantry 120 and the detector part 126 can be attached on the other end of the gantry 120 so that the source and detector parts 124, 126 are opposed from each other.

The source part 124 can comprise an X-ray source in order to emit X-rays (to generate an X-ray beam) for the imaging.

The source can be common for Panoramic and CT imaging modes.

The CT imaging can be Cone beam CT (CBCT) imaging, wherein the beam is a cone-shaped beam, or alternative CT imaging, wherein the beam is a pyramidal-shaped beam, half-moon-shaped cone beam, or other shaped beam.

The detector part 126 can comprise one or two X-ray detectors in order to receive X-rays (the beam) from the source part 124 and to generate image data relating to the object to be imaged, which is then used to form an X.ray image of the object.

A one-detector part 126 can comprise a Panoramic detector, a Panoramic/CT combination detector, a Panoramic/CT/Cephalometric combination detector, or a Panoramic/CT detector, which enables also one-shot Cephalometric imaging.

The one-detector part 126 can be adjustable so that it is possible to rotate and/or to move the detector part 126 relative to the gantry 120 in order to position its detector preferably perpendicularly (towards) to the source.

A two-detector part 126 can comprise a Panoramic detector and a CT detector, or a Cephalometric detector, which enables also Panoramic imaging, and a CT detector.

The two-detectors part 126 can be adjustable so that there are several ways to attach the detectors and it is possible to change a detector that locates within the beam. A used detector is positioned preferably perpendicularly to the source.

Alternatively, the detector part 126 can be fixed.

In addition, the gantry 120 comprises a collimator (X-ray beam limiting) part 128 for the source part 124 in order to collimate the beam from the source part 124.

The collimator part 128 can be attached in front of the source part 124 and it controls a size and shape of the beam during imaging so that the beam matches needs of a selected imaging protocol, selected image size, and related detector size.

In addition, the unit 100 comprises a column 140 in order to support the unit 100, and to adapt its height Z and simultaneously a height of the gantry 120 to a height of a patient 201 for the Panoramic or CT imaging.

The unit 100 comprises a carriage part 145 in order to form a structure, which can provide an up/down Z-movement and a support for other parts that are adapted to be moved at the same time.

The column 140 comprises height adapting part 141 in order to cause the up/down Z-movement for the carriage part 145.

The adapting part 141 can comprise e.g. a height motor, a gear, a threaded rod, and telescopic or counterweighted part in order to realize the Z-movement as a telescopic or counterweighted movement.

The height motor drives the other parts of adapting parts 141 in order to adapt a height of the carriage 145.

In addition, the unit 100 comprises a patient support part 142, 143 in order to support the patient 201 for the Panoramic and CT imaging.

The patient support part can comprise a lower shelf part 142 and a temple support part 143.

The lower shelf 142 can be attached to the carriage part 145.

The lower shelf 142 can support a tip of a chin of the patient 201 and the temple support 143 can support a forehead or temple of the patient 201.

In addition, the unit 100 comprises an upper shelf 150 in order to support the gantry 120 and to enable the gantry 120 to move with respect to the upper shelf 150.

The upper shelf 150 can be attached to the carriage part 145 by a fixed joint.

The gantry 120 can be attached to the upper shelf 150 with attaching means 151 that allow the gantry 120 to rotate around its rotation axis 122 and to move with respect to the upper shelf 150.

The carriage 145 can comprise the lower shelf 142, the temple support 143, the upper shelf 150, and the gantry 120, whereupon, when the height adapting part 141 realizes the Z-movement, height adapting part 141 adapts the height of the parts 142, 143, 150, 120.

FIG. 1b presents how the attaching means 151 can allow a rotational R-movement for the gantry 120 so that the gantry 120 can rotate up to 400 degrees around its rotation axis 122.

The R-movement can be used for Panoramic and/or CT imaging.

In addition, the attaching means 151 can allow a first linear Y-movement for the gantry 120 so that its rotation axis 122 and, thus, its rotation center can be adjusted (positioned) along the Y-movement with respect to the upper shelf 150 before scan movements of the imaging and during the scanning (scan movements with or without irradiation). The Y-movement is parallel to the upper shelf 150.

In addition, the attaching means 151 can allow a second linear X-movement so that the rotation axis 122 can be adjusted within a plane defined by the X- and Y-movements before scan movements of the imaging and during the scanning. The X-movement is perpendicular to the Y-movement.

In addition, the attaching means 151 can allow a third $N_A$-movement, which moves the rotation axis 122 in respect to the gantry 120. The $N_A$-movement of the rotation axis 122 along the beam can be used to change a magnification within the Panoramic and CT imaging modes.

In addition, the attaching means 151 can allow a fourth $N_P$-movement, which moves the rotation axis 122 perpendicular to the beam. It can be used to a change between offset scanning and symmetrical scanning in the CT imaging, whereupon that affects the Field Of View (FOV).

In addition, the unit 100 can comprise a rotating motor part in order to rotate and/or move the gantry 120 as mentioned above by the attaching means 151 during its positioning with respect to the lower shelf 142 so that the gantry 120 is over the lower shelf 142, and/or during scanning.

The rotating motor part can be in the gantry 120 or in the upper shelf 150.

In addition, the unit 100 can comprise a first moving motor part in order to move the collimator part 128 and/or the detector part 126 during positioning of the gantry 120 and/or during the scanning.

The first motor part can be in the gantry part 120 or the upper shelf 150.

The unit 100 can use the R-, X- and Y-, or X- and Y-movements during a scan phase of the Panoramic imaging resulting a Panoramic image.

In addition, the unit 100 can use the R-movement and read out the CT detector during a scan phase of the CT imaging resulting a CT image.

In addition, the unit 100 can use the X and/or Y-movements during the scan phase of the CT imaging.

The unit 100 can produce projection X-ray images of Region Of Interest (ROI) so that a center of ROI and the R-movement coincide. An effective rotation angle (aperture) can be appr. 180-360 degrees depending on the unit 100.

Figure 2B:
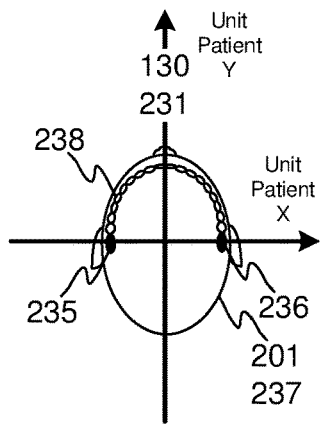
FIG. 2b presents a correctly positioned patient in relation to a co-ordinate system of the unit
Figure 2C:
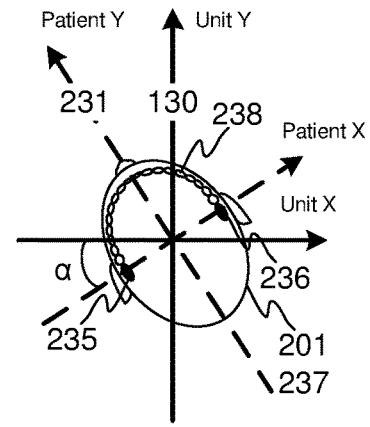
FIG. 2c presents a rotationally mispositioned patient in relation to the co-ordinate system of the unit

FIG. 2a-2c present a X-ray imaging method 202, which can be performed by means of the unit 100.

At a step 203 the unit 100 forms its own co-ordinate system 130 and presents the system 130 in order to use it in a determination of a direction of a head 237 of a patient 201 to be imaged.

At a step 204 the patient 201 is positioned between the source and detector parts 124, 126 so that it is possible to image him/her.

The patient 201 can be positioned by means of the patient support part 142, 143, so that the lower shelf 142 supports his/her tip of a chin and/or the temple support 143 supports his/her forehead or temple.

Alternatively, the patient 201 can be positioned freely, without the aid of the patient support part 142, 143, between the source and detector parts 124, 126.

At a step 205 at least one reference structure 235, 236 of the patient 201 is imaged in order to obtain an image data.

The at least one reference structure 235, 236 can comprise an anatomical or artificial reference structure 235, 236.

The anatomical reference structure 235, 236 can comprise temporomandibular joint (TMJ), edge of ramus 235, 236, or ear canal of the head 237 of the patient 201.

The artificial reference structure can comprise e.g. a bite plate, a bite stick, or a marker to be attached directly or indirectly to the patient 201.

In addition, the at least one reference structure 235, 236 can comprise two anatomical reference structures 235, 236, which comprise temporomandibular joints, edges of ramus 235, 236, or ear canals.

After the gantry 120 has been moved (driven) by means of the at least one movement presented in context of FIG. 1a-1b to a first starting position of the scanning, the source and detector parts 124, 126 are controlled in order to image the at least one reference structure 235, 236.

Alternatively, in addition to the control of the source and detector parts 124, 126, the gantry 120 can be moved during scanning by means of the at least one aforementioned movement in order to image the at least one reference structure 235, 236.

When the gantry 120 do not move during the scanning, the first starting point is a first finishing point at the same time, and when the gantry 120 moves during scanning, the first finishing point differs from the first starting point.

The result of the scanning is the image data captured by the detector part 126, which can comprise one or plurality of image data.

At a step 208 an occurrence of the at least one reference structure 235, 236 is determined 208 from the captured image data and, then, it is possible to determine a position of each occurring reference structure 235, 236 from the image data.

At a step 210, a co-ordinate system 231 for the patient 201 can be formed on a grounds of the determined position of the each reference structure 235, 236.

The co-ordinate system 231 indicates e.g. a lateral direction of the head 237 of the patient 201. The lateral direction of the head 237 can be a direction where a face of the patient 201 is directed.

At a step 212 a position of the head 237 is determined by means of e.g. its lateral direction, which basis on the determined occurring at least one reference structure 235, 236.

The lateral direction of the head 237 can be determined in relation to the unit so that a rotational displacement (angle) a between the formed co-ordinates systems 130, 231 of the unit 100 and the patient 201 is determined. The displacement a determines a deviation (relation) of the co-ordinates systems 130, 231.

If the head 237 of the patient is correctly positioned at the step 204 and he/she has not moved his/her head 237, the co-ordinates systems 130, 231 are parallel according to FIG. 2b and there is no displacement a. If, for one, the head 237 is incorrectly positioned and/or he/she has rotated the head 237 after the positioning, the co-ordinates systems 130, 231 are not parallel and there exists some deviation between directions of the co-ordinates systems 130, 231 according to FIG. 2c.

At a step 213, the position of the head 237 is determined e.g. in relation to the gantry 120.

At a step 214 at least one imaging movement of the source and detector parts 124, 126, with respect to the patient 201, is determined on a grounds of the relationship between the determined position of the head 237 and the gantry 120.

If the co-ordinates systems 130, 231 are parallel, i.e. there is no rotational deviation between the co-ordinates systems 130, 231, the unit can provide the actual imaging (scanning) of the patient 201 according to at least one predetermined, the one aforementioned movement of the source and detector parts 124, 126.

If, for one, the co-ordinates systems 130, 231 are not parallel, i.e. there is some rotational deviation between the co-ordinates systems 130, 231, the unit calculates, by means of the determined rotational displacement a, at least one imaging (scan) movement, which takes the determined deviation into account and helps to avoid failures in resulted image data, which are caused by a rotational mispositioning of the patient 201.

The at least one calculated imaging movement is provided by means of the at least one aforementioned movement of the source and detector parts 124, 126.

In addition to the correction of the rotational misposition, there is possibility to correct an occurred transitional misposition of the patient 201 before scan movements of the actual imaging.

The correction of an occurred transitional misposition can be made in the Panoramic imaging by a previously-known autofocus feature.

In addition, the correction of the occurred transitional misposition can be made in the Panoramic imaging when it is used a FF-Panoramic imaging system, which is capable of two-dimensional linear movements.

At a step 216, the patient 201 is imaged in order to obtain an image data, which is then used to form or to reconstruct at least one X-ray image of the patient 201.

The actual scanning at the step 216 is provided by the at least one imaging movement of the source and detector parts 124, 126 determined at the step 214.

The gantry 120 can start its at least one aforementioned, imaging movement from a second starting position, which is the same point as the first starting position, if it did not move during the scanning of the at least one reference structure 235, 236.

Alternatively, the gantry 120 can start the at least one aforementioned imaging movement from a second starting position, which corresponds the first finishing point to which the gantry stopped after making the at least one movement during the scanning of the at least one reference structure 235, 236.

During the actual scanning, the gantry 120 is moved according to the at least one determined imaging movement, and the source and detector parts 124, 126 are controlled in order to obtain the image data of the patient 201.

After the obtaining of the image data in step 216, an image is formed from the obtained image data. If it is used a Panoramic or Cephalometric imaging mode, then, the image is formed to a 2-dimensional (2D) image. If it is used a CT imaging mode, then, the image is reconstructed to 3-dimensional (3D) volume.

The formation (or reconstruction) of the image is performed by the processor part, which can locate in the unit 100 or it can be in a separate attached device, e.g. a computer or a tablet computer.

Figure 3:
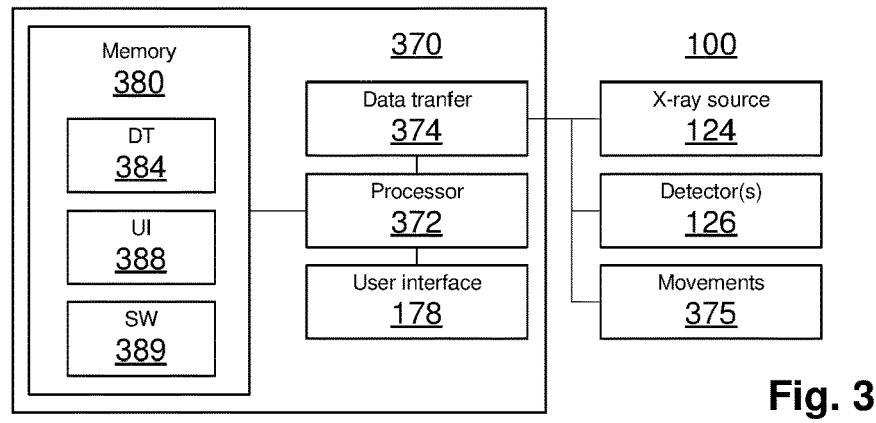
FIG. 3 presents functional parts of the unit

FIG. 3 presents functional parts of the unit 100.

The unit 100 comprises a control part 370 in order to control the unit 100, and its aforementioned movements and imaging processes.

The control part 370 comprises a processor part 372 in order to perform user and/or computer program (software) initiated instructions, and to process data.

The processor part 372 can comprise at least one processor.

If the processor part 372 comprises several processors, the processors can locate merely in the unit 100 or in at least one separate device, or so that one part of the processors locates in the unit 100 and another part of the processors locates in the at least one separate device that is configured to perform the formation or reconstruction of the image.

In addition, the control part 370 can comprise a memory part 380 in order to store and to maintain data. The data can be instructions, computer programs, and data files.

The memory part 380 can comprise at least one memory.

In addition, the control part 370 can comprise a data transfer part 374 in order to send control commands to at least one of the source part 124, detector part 126, and a movement part 375.

The movement part 375 can comprise motors, drivers, or other parts 375 that cause the movements of at least one of the part 120, 124, 126, 128, 141, 162, 164, 166.

In addition, the data transfer part 374 can receive data from measuring parts or other detection parts that detect the function of the unit 100.

In addition, the data transfer part 374 can send control commands to at least one of the parts 124, 126, 375.

In addition, the data transfer part 374 can receive information from at least one of the parts 124, 126, 375.

In addition, the control part 370 can comprise a user interface part 178 in order to input control commands, to receive information and/or instructions, and to display information.

The UI part 178 can comprise at least one of a touchscreen, at least one function key, and a wired or wireless remote controller.

The UI part 178 can be attached to the column 140 or carriage 145.

The memory part 380 can comprise at least a data transfer application 384 in order to control the data transfer part 374, a user interface application 388 in order to control the UI part 178, and a computer program (code) 389 in order to control the function of the unit 100.

The computer program 389 can control at least one of the movement part 375, detection devices, the source part 124, and the detector part 126.

In addition, the computer program 389 can control imaging parameters, imaging sizes, and imaging modes.

The memory part 380 and the computer program 389, with the processor part 372, can cause the unit 100 at least to provide actions presented in context of the figures.

Such action can be controlling the source part 124 and the detector part 126 in order to obtain an image data.

In addition, such action can be determining the at least one reference structure 235, 236 of the patient 201 from the image data.

In addition, such action can be determining a position of a head 237 of the patient 201 on a grounds of the at least one reference structure 235, 236.

In addition, such action can be determining at least one imaging movement of the source and detector parts 124, 126 with respect to the patient 201 on a grounds the determined position of the head 237 for the imaging of the patient 201.

The computer program 389 can be a computer program product that comprises a tangible, non-volatile (non-transitory) computer-readable medium bearing a computer program code 389 embodied therein for use with a computer (control part 370).

The method 202 fixes two of the most common errors in the positioning of patient 201 unlike the known imaging methods, whereupon the translational and rotational errors can be corrected before the actual imaging of the object when scan movements are adjusted in view of the actual position and angulation of the head 237 of the patient 201.

In addition, the method 202 decreases a number of re-taking of images and allows grater tolerances in the positioning of the patient 201.

The invention claimed is:

1. An X-ray imaging unit for X-ray imaging comprising
a processor,
a gantry,
an X-ray source for emitting X-rays, and
an X-ray imaging detector for receiving the X-rays from the source,
wherein the gantry comprises the X-ray source and the X-ray imaging detector, and
wherein the processor is configured to
control the X-ray source and the X-ray imaging detector in order to obtain image data,
detect an occurrence of at least one anatomical reference structure of a patient in the obtained image data,
determine a position of a head of the patient relative to the gantry based at least in part on the detected occurrence of the at least one anatomical reference structure in the image data, and
adjust a movement trajectory of the X-ray source and the X-ray imaging detector while imaging the patient based on the determined position of the head of the patient relative to the gantry.

2. The unit of claim 1, wherein the processor is further configured to determine a position of each reference structure detected in the image data.

3. The unit of claim 1, wherein the determination of the position of the head comprises a determination of a direction of the head of the patient in relation to the X-ray imaging unit.

4. The unit of claim 1, wherein the processor is configured to adjust the movement trajectory of the X-ray source and the X-ray imaging detector based on the determined position of the head of the patient relative to the gantry by
    determining at least one imaging movement of the X-ray source and the X-ray imaging detector with respect to the patient based on the relationship between the determined position of the head and the gantry, and
    controlling the movement of the X-ray source and the X-ray imaging detector according to the determined at least one imaging movement,
    wherein the processor is further configured to obtain at least one X-ray image of the patient while controlling the movement of the X-ray source and the X-ray imaging detector.

5. The unit of claim 1, wherein the at least one anatomical reference structure comprises temporomandibular joint, edge of ramus, or ear canal of the head of the patient.

6. The unit of claim 5, wherein the at least one anatomical reference structure comprises two anatomical reference structures, which comprise temporomandibular joints, edges of ramus, or ear canals.

7. The unit of claim 1, further comprising a patient support for supporting the patient to be imaged during imaging.

8. The unit of claim 1, which is configured to perform panoramic or computed tomography imaging.

9. The unit of claim 1, wherein the processor is further configured to determine a positioning error of the patient based on the determined position of the head of the patient relative to the gantry, and
    wherein the processor is configured to adjust the movement trajectory of the X-ray source and the X-ray imaging detector based on the determined position of the head of the patient relative to the gantry by adjusting the movement trajectory of the X-ray source and the X-ray imaging detector based on the determined positioning error of the patient.

10. The unit of claim 9, wherein the positioning error includes at least one selected from a group consisting of a translational positioning error and a rotational positioning error.

11. The unit of claim 1, wherein the processor is configured to adjust the movement trajectory of the X-ray source and the X-ray imaging detector based on the determined position of the head of the patient relative to the gantry by adjusting a rotational axis of the gantry based on the determined position of the head of the patient.

12. The unit of claim 1, wherein the processor is further configured to detected a change in the position of the head of the patient during an imaging scan based on the determined position of the head of the patient, and
    wherein the processor is configured to adjust the movement trajectory of the X-ray source and the X-ray imaging detector based on the determined position of the head of the patient by adjusting the movement trajectory of the X-ray source and the X-ray imaging detector during the imaging scan to correct for the detected change in the position of the head of the patient during the imaging scan.

13. An X-ray imaging unit for X-ray imaging comprising:
    a processor,
    a gantry,
    an X-ray source for emitting X-rays, and
    an X-ray imaging detector for receiving the X-rays from the source,
    wherein the gantry comprises the X-ray source and the X-ray imaging detector, and
    wherein the processor is configured to
        control the X-ray source and the X-ray imaging detector in order to obtain image data,
        detect an occurrence of at least one anatomical reference structure of a patient in the obtained image data,
        determine a position of each reference structure detected in the image data, and
        form a co-ordinate system for the patient based on the determined position of each anatomical reference structure, which co-ordinate system of the patient indicates a direction of the head of the patient.

14. An X-ray imaging unit for X-ray imaging comprising:
    a processor,
    a gantry,
    an X-ray source for emitting X-rays, and
    an X-ray imaging detector for receiving the X-rays from the source,
    wherein the gantry comprises the X-ray source and the X-ray imaging detector, and
    wherein the processor is configured to
        control the X-ray source and the X-ray imaging detector in order to obtain image data,
        detect an occurrence of at least one anatomical reference structure of a patient in the obtained image data,
        determine a position of a head of the patient relative to the gantry based at least in part on the detected occurrence of the at least one anatomical reference structure in the image data,
            wherein the determination of the position of the head comprises a determination of a direction of the head of the patient in relation to the X-ray imaging unit, and
        present a co-ordinate system for the unit, wherein the determination of the direction of the head in relation to the unit comprises a determination of a rotational displacement between the co-ordinates systems of the unit and the patient.

15. A method for X-ray imaging by an X-ray imaging unit, the X-ray imaging unit including a gantry, an X-ray source for emitting X-rays, an X-ray imaging detector for receiving the X-rays form the source, wherein the gantry comprises the X-ray source and the X-ray imaging detector, the method comprising steps of
    controlling the X-ray source and the X-ray imaging detector in order to obtain the image data,
    detecting an occurrence of at least one anatomical reference structure of a patient in the obtained image data,
    determining a position of a head of the patient based at least in part on the detected occurrence of the at least one reference structure in the image data, and
    adjusting a movement trajectory of the X-ray source and the X-ray imaging detector while imaging the patient based on the determined position of the head of the patient.

16. A tangible non-volatile computer-readable medium storing computer-readable instructions of a computer program for X-ray imaging that, when executed by a processor, perform the method of claim 15.

17. The method of claim 15, further comprising determining a positional error of the patient based on the determined position of the head of the patient, and wherein adjusting the movement trajectory of the X-ray source and the X-ray imaging detector based on the determined position of the head of the patient includes adjusting the movement trajectory of the X-ray source and the X-ray imaging detector based on the determined positioning error of the patient.

18. The method of claim 15, wherein adjusting the movement trajectory of the X-ray source and the X-ray imaging detector based on the determined position of the head of the patient includes adjusting a rotational axis of the gantry based on the determined position of the head of the patient.

* * * * *